United States Patent [19]
Schwiegk et al.

[11] Patent Number: 5,182,005
[45] Date of Patent: Jan. 26, 1993

[54] REFERENCE ELECTRODE FOR CHEMICAL SENSORS

[75] Inventors: Stefan Schwiegk; Klemens Mathauer, both of Mainz; Gerhard Wegner, Mainz-Drais; Bernd F. W. Hoffmann, Rheinstetten; Albrecht Vogel, Karlsruhe, all of Fed. Rep. of Germany

[73] Assignee: BASF Aktiengesellschaft, Ludwigshafen

[21] Appl. No.: 705,441

[22] Filed: May 24, 1991

[30] Foreign Application Priority Data

Jun. 2, 1990 [DE] Fed. Rep. of Germany ....... 4017805

[51] Int. Cl.[5] ............................................. G01N 27/26

[52] U.S. Cl. ................................... 204/435; 204/416; 204/418; 204/433

[58] Field of Search ............... 204/435, 433, 418, 416; 435/177

Primary Examiner—John Niebling
Assistant Examiner—Bruce F. Bell
Attorney, Agent, or Firm—Keil & Weinkauf

[57] ABSTRACT

The invention relates to a reference electrode for chemical sensors based on ion-selective field-effect transistors (CHEMFETs) in an electrolyte/insulator/semiconductor system. The reference electrode is essentially composed of a polyglutamate-coated insulator/semiconductor substrate or of a polyglutamate-coated phthalocyaninato-polysiloxane polymer film applied to an insulator/semiconductor substrate.

6 Claims, 7 Drawing Sheets

REFERENCE ELECTRODE FOR CHEMICAL SENSORS

The present invention relates to a reference electrode for chemical sensors based on ion-selective field-effect transistors (CHEMFETs) which contain thin films on insulator/semiconductor substrates in an electrolyte/insulator/semiconductor (EIS) system. This reference electrode can be produced in an advantageous manner and can also be employed as an integrated component in an EIS system.

The design of integrated chemical sensors based on ion-selective field-effect transistors is known and is described, for example, by J. Janata and R. J. Huber in Solid State Chemical Sensors, Academic Press, New York, 1985, Ch. 2, p. 66 and Ch. 3, and by A. Sibbald, Recent advances in field-effect chemical microsensors, J. Mol. Electron., 2 (1986) 51-83. The use of CHEMFETs as online sensors for monitoring chemical processes is prevented by some still unsolved problems, especially by inadequate long-term stability and low adhesion of the chemically sensitive layer. Some years ago, Langmuir-Blodgett films (LB films) (cf. J. Am. Chem. Soc., 57 (1935) 1007-1022) were proposed as alternative to the customarily used conventionally applied polymers such as PVC or polyvinyl alcohol (cf. G. G. Roberts, An applied science perspective of Langmuir-Blodgett films, Adv. Phys., 34 (1985) 1-38). However, conventional LB films of amphiphilic substances have the same stability problems. Recently, LB films of phthalocyaninato-polysiloxane polymers were found to be a material which, as the ion-sensitive component in electrolyte/insulator/semiconductor structures, has proven to be very advantageous in terms of long-term stability and sensitivity for protons and displays no cross-sensitivity for alkali metal ions (cf. A. Vogel, B. Hoffmann, Th. Sauer and G. Wegner: Langmuir-Blodgett Films of Phthalocyaninato-Polysiloxane Polymers as a novel Type of CHEMFET Membrane; Sensors and Actuators, Vol. B1 (1990) pp. 408-412; Elsevier Sequoia/Printed in the Netherlands).

It is an object of the present invention to indicate a reference electrode suitable for this system. We have found that this object is achieved, surprisingly, by either coating the insulator/semiconductor substrate directly with a polyglutamate or providing a polyglutamate coating on a phthalocyaninato-polysiloxane polymer film applied to an insulator/semiconductor substrate.

The present invention therefore relates to a reference electrode for chemical sensors based on ion-selective field-effect transistors (CHEMFETs) which contain insulator/semiconductor substrates as such or coated with thin films of phthalocyaninato-polysiloxane polymers in an electrolyte/insulator/semiconductor system, wherein the reference electrode is essentially composed of a polyglutamate-coated insulator/semiconductor substrate or of a polyglutamate-coated phthalocyaninato-polysiloxane polymer film which is applied to an insulator/semiconductor substrate.

To produce the novel reference electrode, the polyglutamate is preferably applied by the Langmuir-Blodgett technique to the insulator/semiconductor substrate or to the phthalocyaninato-polysiloxane polymer film applied to an insulator/semiconductor substrate.

The polyglutamate which is preferably employed is a poly($\gamma$-methyl L-glutamate) or, when the Langmuir-Blodgett technique is used, especially a poly($\gamma$-methyl L-glutamate-co-$\gamma$-n-alkyl L-glutamate) where n-alkyl is $C_{10}H_{21}$ to $C_{25}H_{51}$ and the n-alkyl L-glutamate content is from 20 to 40%.

It is additionally preferred to apply the polyglutamate in a thickness of from 3.6 to 180 nm, in particular 7.2 to 54 nm, to the insulator/semiconductor substrate or to the phthalocyaninato-polysiloxane polymer film.

A suitable and preferred insulator/semiconductor substrate is an $SiO_2/Si$ substrate.

It is particularly advantageous to employ the novel reference electrode as an integrated component of an insulator/semiconductor substrate, especially of an $SiO_2/Si$ substrate, which is as such or is coated with an ion-sensitive film, for example with a phthalocyaninato-polysiloxane polymer film, in an EIS system.

A particular feature of the novel reference electrode is that it has the same construction as an EIS sensor system, differing only in that the sensitive layer of the sensor system is replaced by the ion-insensitive polyglutamate film. This allows EIS systems to be considerably simplified and to be used for controlling chemical processes.

Details of the construction of the novel reference electrodes follow.

Figure 7:
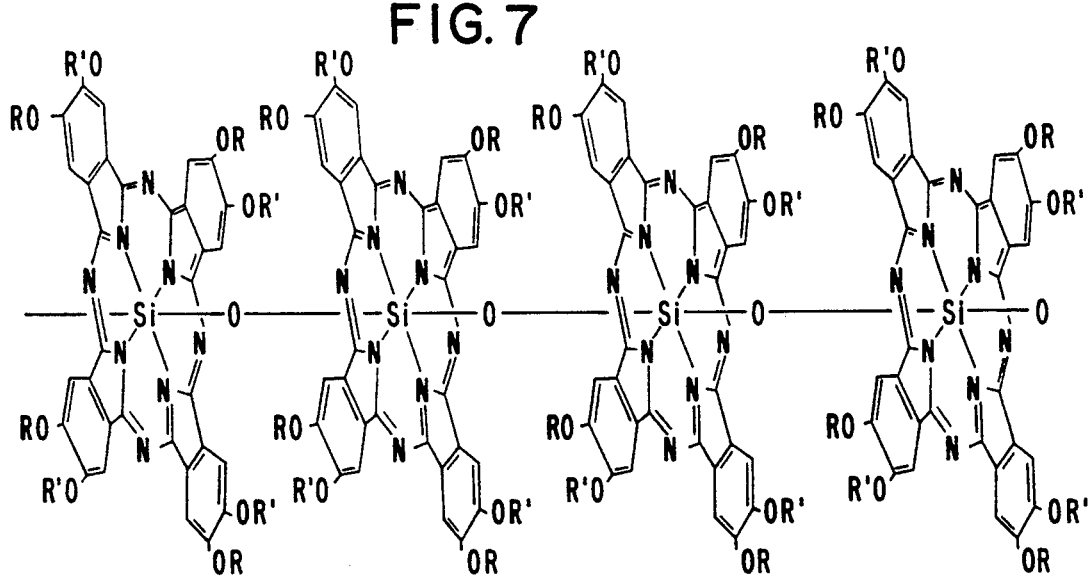

FIG. 7 shows diagrammatically the construction of a phthalocyaninato-polysiloxane sequence where R is $C_nH_{2n+1}$ with n=1 to 5 and R' is $C_nH_{2n+1}$ with n=5 to 10, preferably with the proviso that R≠R'; for example R=methyl, R'=octyl. The phthalocyaninato-polysiloxane polymer film can be applied in a thickness of, for example, from 2 to 200 nm to the insulator layer of the EIS system by spincoating or, preferably, by the Langmuir-Blodgett technique.

The Langmuir-Blodgett technique, the apparatus suitable for it and the requirements for this method to be applicable are known and are described, for example, in G. L. Gaines, "Insoluble Monolayers at Liquid-Gas-Interfaces", Interscience Publishers, 1966.

When the Langmuir-Blodgett technique is used, the phthalocyaninato-polysiloxane is generally spread as a dilute solution (0.001 to 0.5% strength), for example as 0.05% strength solution in a halohydrocarbon such as chloroform, on an aqueous subphase in a Lauda film balance and further processed in a conventional manner (evaporation of the solvent, compression to a surface tension of 25 mN/m until a constant film area is reached and subsequent transfer of the required number of monolayers by introducing and removing the substrate to be coated.

Figure 8:
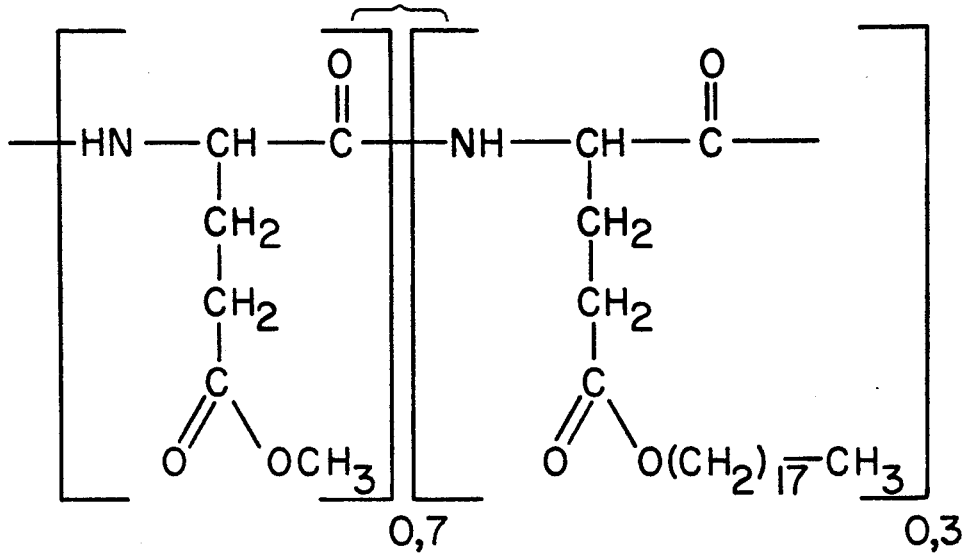

FIG. 8 shows as example of a preferred polyglutamate poly(γ-methyl L-glutamate-co-γ-n-octadecyl L-glutamate) which contains 70 mol % γ-methyl L-glutamate units and 30 mol % γ-n-octadecyl L-glutamate units. Other preferred poly(γ-methyl L-glutamate-co-γ-n-alkyl L-glutamates) are those where n-alkyl is $C_{10}H_{21}$ to $C_{25}H_{51}$ and the n-alkyl L-glutamate content is from 20 to 40 mol %. These copolyglutamates can have any degree of polymerization but preferably have a degree of polymerization of from 20 to 2000, with a helical structure being preferred. These copolyglutamates can be applied to the substrates particularly advantageously using the Langmuir-Blodgett technique. For this purpose, they are generally dissolved in suitable organic solvents, preferably in halohydrocarbons such as chloroform, with the polyglutamate concentration in the solvent expediently being from 0.001 to 0.1%, for example about 0.02%. A Lauda film balance is also used in the case of the copolyglutamates, generating a clean room atmosphere in a laminar flow cabinet. The copolyglutamate solution is spread on a pure water subphase at constant temperature and, after the solvent has evaporated off, compressed to a surface tension of 20 mN/m and, after a constant film area has been reached, the substrate which is to be coated is expediently immersed through the polymer film into the subphase using a Lauda film lift operating at 10 mm/min. One monolayer is transferred on each introduction and removal. After the required number of monolayers, which can be from 10 to 30, has been transferred, the substrate is dried and heated if necessary. Where homopolyglutamates, which are likewise suitable, such as poly(γ-methyl L-glutamate) or poly(γ-benzyl L-glutamate) are employed for coating the insulator/semiconductor substrate which is as such or is provided with a phthalocyaninato-polysiloxane polymer film, this is expediently carried out by spincoating at from 500 to 2000 rpm and subsequent removal of the solvent. Layers of appropriate thinness and effectiveness can be generated in this way too.

The preparation of suitable polyglutamates and copolyglutamates is to be found, for example, in EP-A 03 00 420.

Thus the polyglutamates can be applied by spin-coating from their solutions or, preferably, by the Langmuir-Blodgett technique to the insulator layer, which is as such or coated with a phthalocyaninato-polysiloxane polymer film, of the EIS system. The thickness of the polyglutamate layer can be from 3.6 to 180, preferably 7.2 to 54 nm.

The polyglutamate layers applied according to the invention adhere well and resist oxidation. The novel reference electrode is particularly suitable for constructing, together with a pH-sensitive EIS structure (EIS capacity or ISFET) produced by the same technology, an integrated pH sensor.

Figure 4:
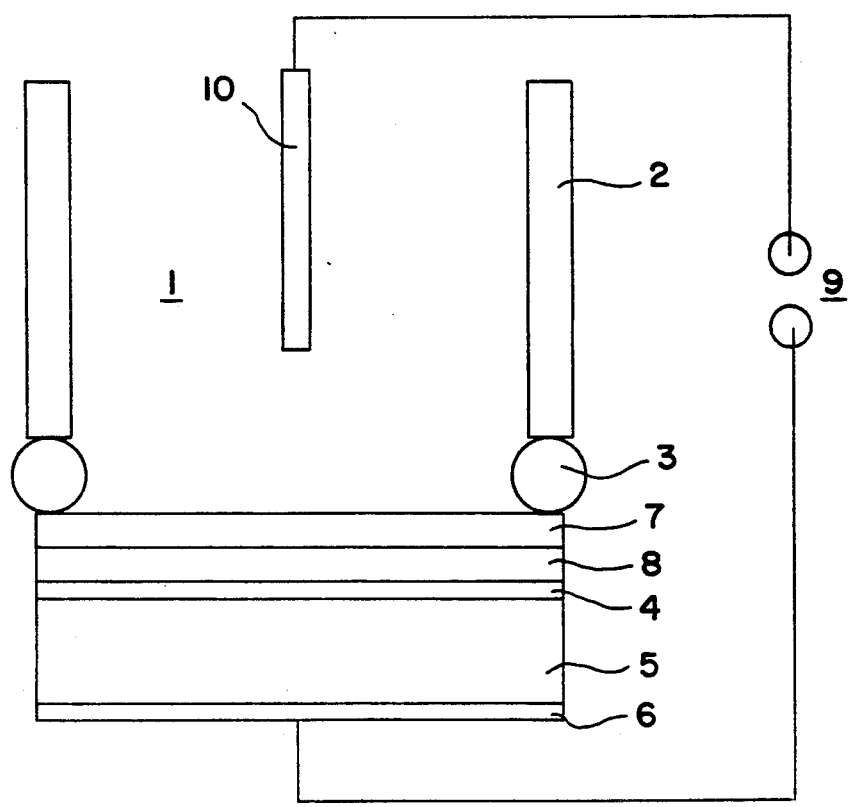
FIG. 4 shows diagrammatically the arrangement for testing an EIS system shown in FIG. 3 by measurement with a conventional Ag/AgCl reference electrode, where 9 is the electrical contact for measuring the capacitance at various bias voltages (C/U plots) and 10 is the silver/silver chloride reference electrode.
Figure 5:
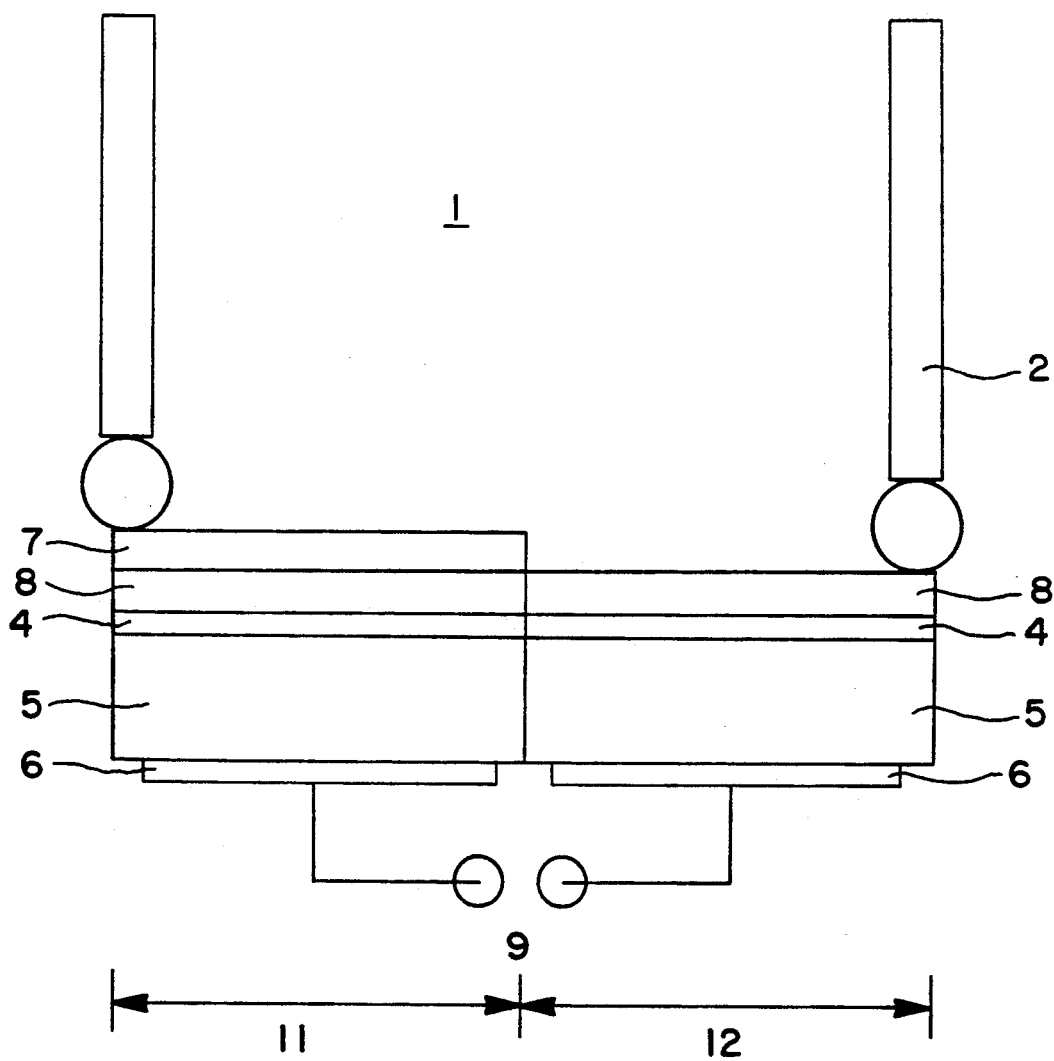
FIG. 5 shows diagrammatically pH-sensitive and reference EIS systems combined in series, where 11 is the reference part of the EIS system and 12 is the pH-sensitive part of the EIS system.
Figure 6:
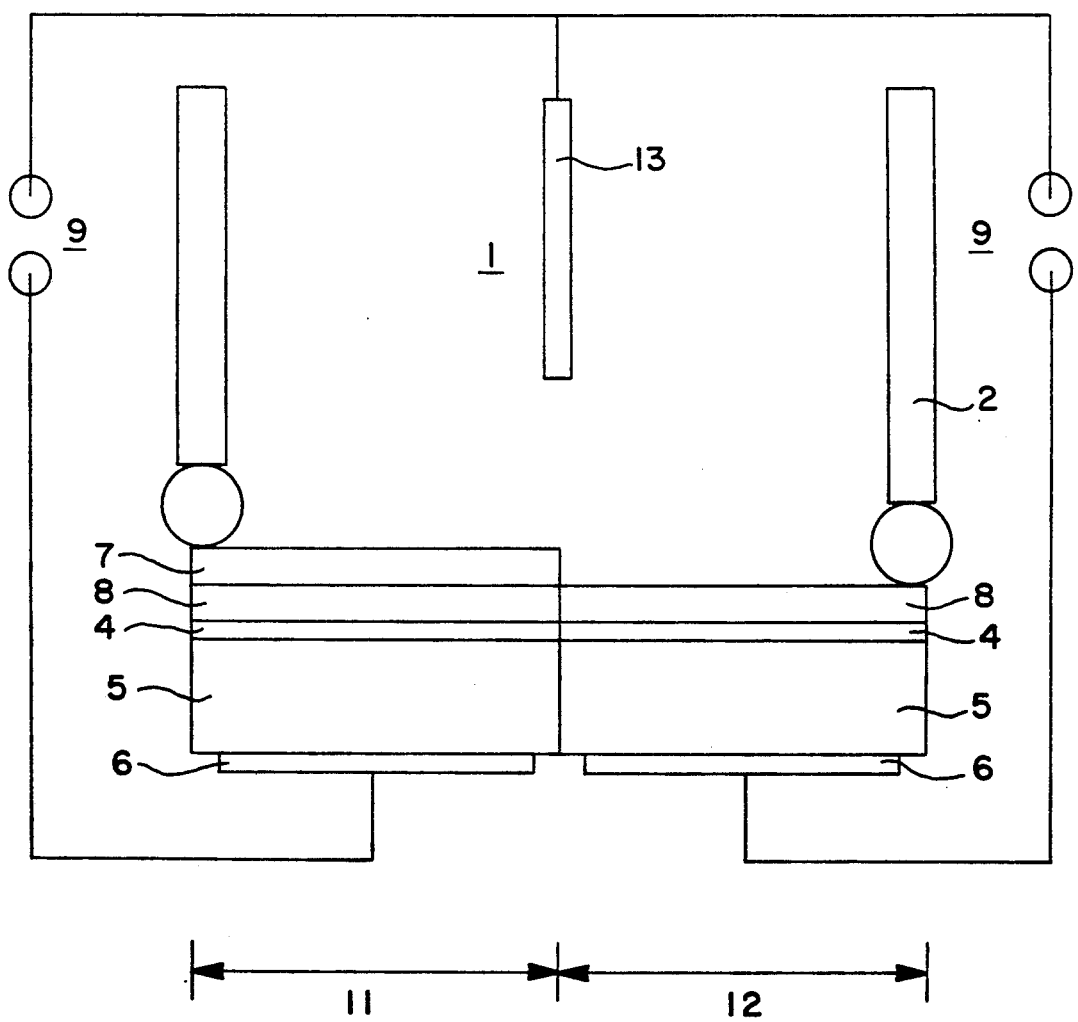
FIG. 6 shows diagrammatically pH-sensitive and reference EIS systems combined in parallel, where 1 to 12 have the abovementioned meanings and 13 is a platinum wire dipping into the electrolyte.
Figure 9:
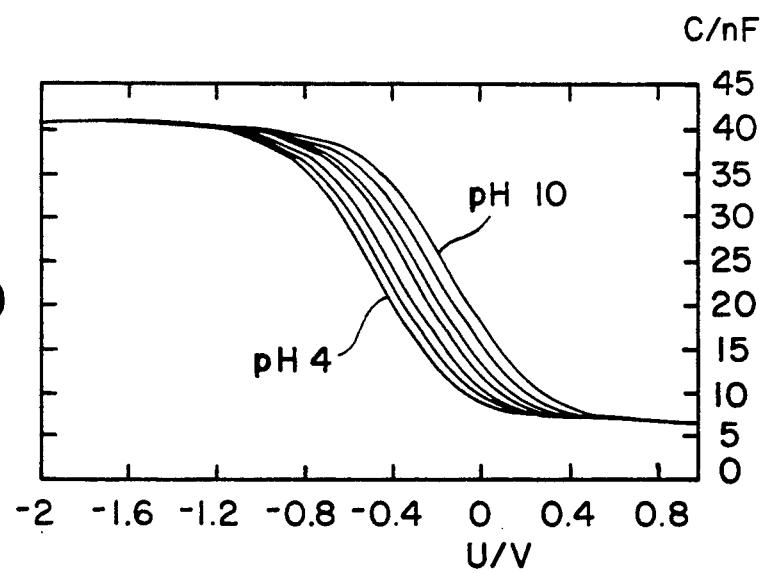

FIG. 9 shows the C/U plots (measured in nF/V) as a function of the pH of the electrolyte solution in an EIS system shown in FIG. 4 with 20 LB layers of phthalocyaninato-polysiloxane (8) but without polyglutamate layer (7).

Figure 10:
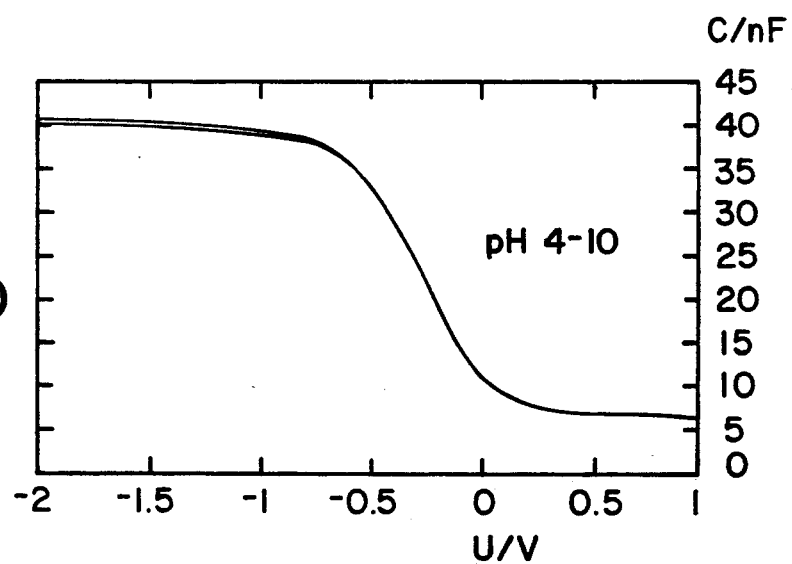

FIG. 10 shows the C/U plots (measured in nF/V) as a function of the pH of the electrolyte solution in an EIS system shown in FIG. 4 with 20 LB layers of polyglutamate (7) but without phthalocyaninato-polysiloxane (8).

Figure 11:
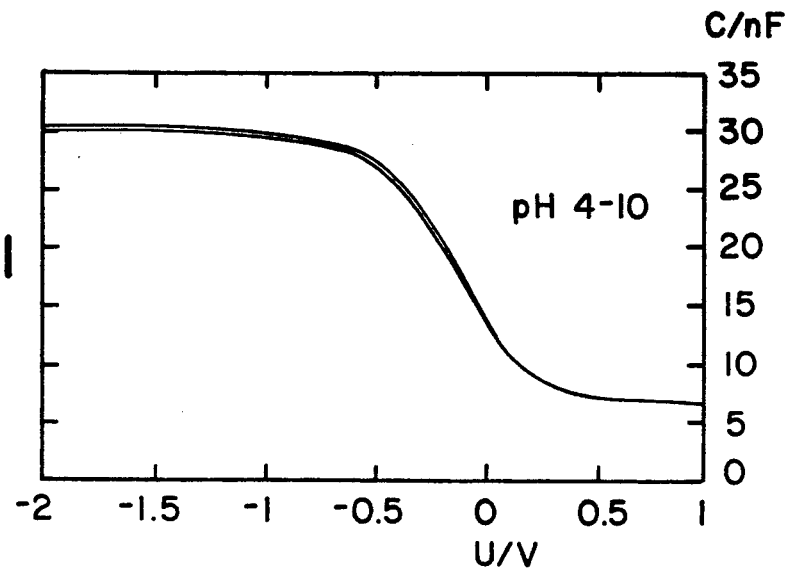

FIG. 11 shows the C/U plots (measured in nF/V) as a function of the pH of the electrolyte solution in an EIS system shown in FIG. 4 where the insulator layer (4) has initially been coated with 12 LB layers of phthalocyaninato-polysiloxane polymer (8) and then covered with 30 LB layers of polyglutamate (7).

Figure 12:
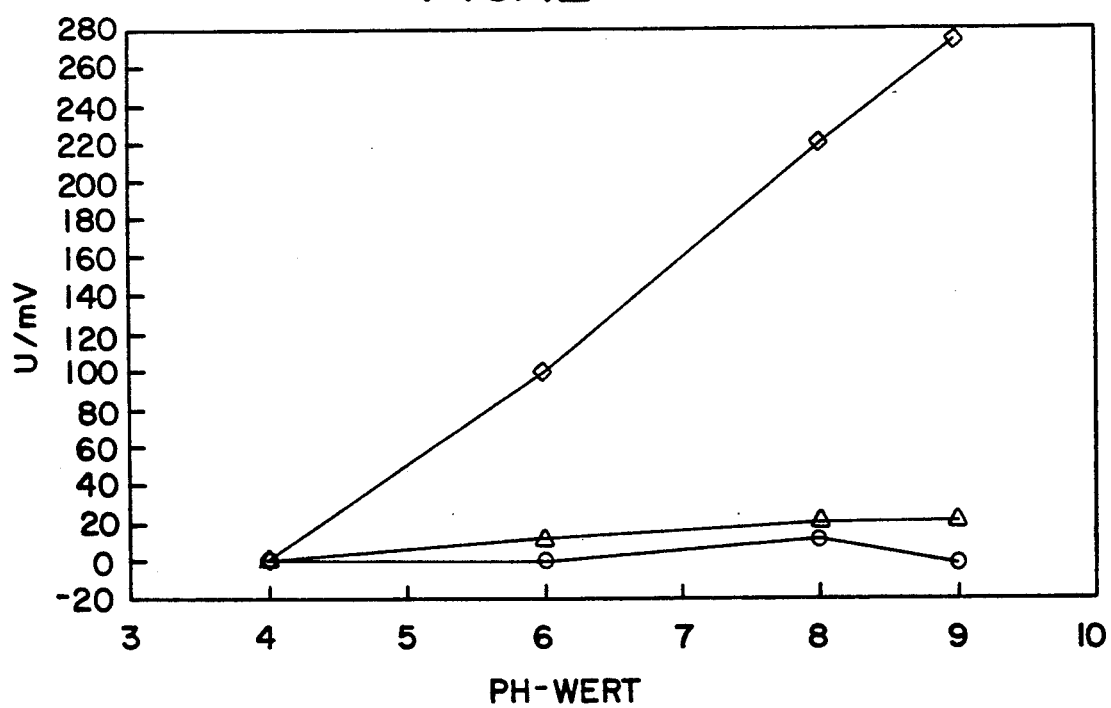

FIG. 12 shows the pH sensitivity of various EIS systems. In this, is the EIS system of FIG. 9; is the EIS system of FIG. 10; O is the EIS system of FIG. 11.

Suitable semiconductor/insulator substrates for the novel reference electrodes are silicon/$SiO_2$, $Si_xN_y$/$SiO_2$ (preferably with x=3 and y=4), $ZrO_2$/$SiO_2$, germanium/$GeO_2$ and III-V semiconductors such as GaAs, GaInP with insulating layers in place of an oxide. The preferred semiconductor/insulator substrate is Si/$SiO_2$, in particular p-silicon/$SiO_2$, for example p-doped silicon wafers with a specific resistance of from 17 to 30 Ω.cm with an $SiO_2$ layer 50±5 nm thick.

The particular advantages of the novel reference electrode are that it is pH-insensitive, mechanically insensitive and can be miniaturized and its production is compatible with standard silicon technology. The novel reference electrode thus makes it possible to construct integrated pH sensors and to measure pH at low temperatures (T<0° C.).

Parts and percentages in the examples are by weight unless otherwise specified.

EXAMPLE 1

Preparation of a reference EIS structure with a polyglutamate film:

p-Doped silicon wafers with a specific resistance of 17-30 Ω.cm with an $SiO_2$ layer 50±5 nm thick were used. The sample size was 15×15 mm. To clean the wafers they were treated successively with the following solutions in an ultrasonic bath, in each case at 40° C.: initially with acetone to remove the photoresist (10 minutes); they were then rinsed with pure water and subsequently treated with a mixture of $H_2SO_4$, $H_2O_2$ and $H_2O$ in the ratio 1:1:5 (10 minutes), rinsed with pure water, then treated with a mixture of 25% strength $NH_3$ and 30% strength $H_2O_2$ in the ratio 1:1:5 (60 minutes), rinsed with pure water, then treated with 10 % strength HCl (2 minutes), rinsed with pure water and finally dried in an oven at 50° C.

The chemicals used for this were analytical grade, and the pure water was obtained from a Seral pro 90 C system.

To render the wafers hydrophobic, the cleaned substrates were silanized in a 40% strength solution of hexamethyldisilazane in chloroform at 40° C. for 10 minutes.

Production of the LB layer:

A Lauda film balance was used, generating a clean room atmosphere in a laminar flow cabinet. An external thermostat kept the subphase of pure water at 18° C. The polyglutamate[poly(γ-methyl L-glutamate-co-γ-n-octadecyl L-glutamate) degree of polymerization 2000] was spread using a very dilute solution (0.02% strength) in chloroform. After compression to a surface tension of 20 mN/m the film was left until the area was constant. The substrate was then immersed, using a film lift operating at 10 mm/min, through the polymer film into the subphase. One monolayer was transferred on each introduction and removal in this way. After 30 monolayers had been transferred the substrate was dried.

The polyglutamate film was then heated at 100° C. for 30 minutes and the metal coating was applied; this entailed the polyglutamate film being removed from the silicon wafer on the p-silicon side which was then metalized by deposition of aluminum and gold vapors successively.

Figure 1:
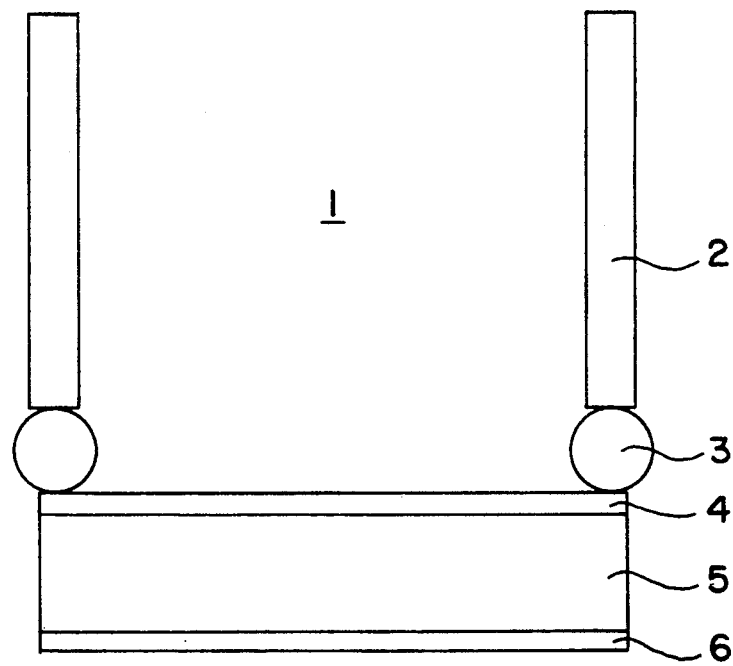
FIG. 1 shows diagrammatically the principle of the construction of an EIS system: 1=electrolyte; 2=electrolyte vessel; 3=seal; 4=insulator (eg. $SiO_2$); 5=semiconductor (eg. p-silicon); 6=metalization (eg. gold or aluminum).
Figure 2:
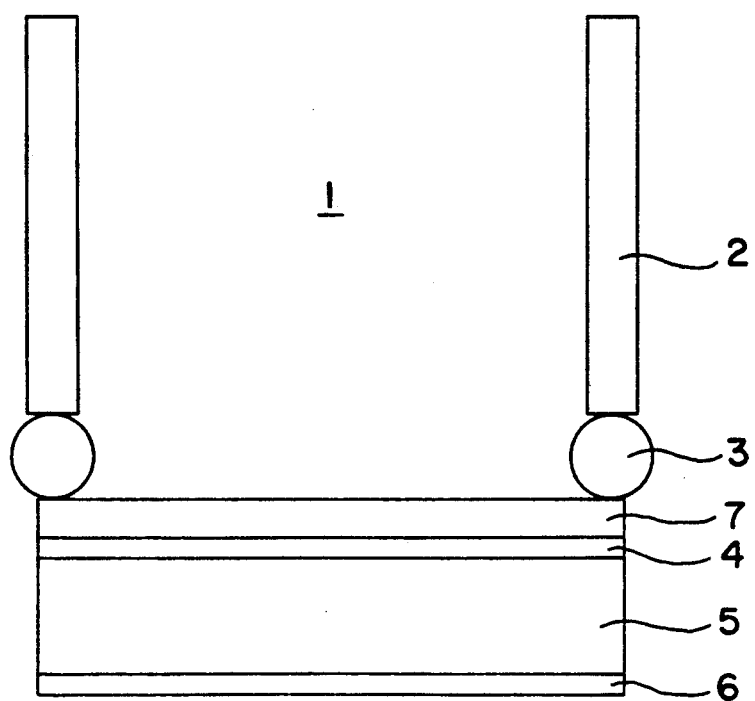
FIG. 2 shows diagrammatically a novel EIS system where 7 is the polyglutamate film and 1 to 6 have the meanings indicated for FIG. 1.
Figure 3:
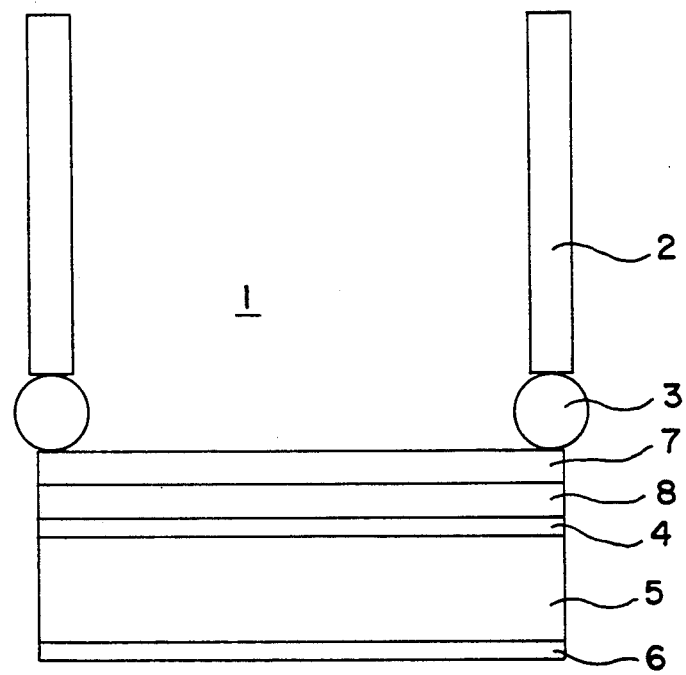
FIG. 3 shows diagrammatically another novel EIS system where 8 is the phthalocyaninato-polysiloxane film which is covered with a polyglutamate film 7.

Construction for measurement:

The measurement cell comprised a Teflon vessel containing about 1 ml of electrolyte (cf. FIG. 1 and FIG. 2). The reference electrode was an Ag/AgCl/1 M KCl microreference electrode supplied by Ingold. The entire construction was installed in a metal protective box with coaxial cables for connection to the measuring instruments.

The C/U plots were constructed using a Hewlett-Packard 4272A LCR meter. The bias voltage covered the range from $-2$ to $+1$ volt in steps of 50 mV. The capacitance was measured by a superimposed AC voltage (10 mV, 1 kHz). The experiment was controlled with an Apple II microcomputer.

The measurement procedure was as follows:

The measured electrolyte solutions were commercial standard pH buffer solutions to which 0.1 mol/l KCl had been added as conducting salt. Examples of suitable buffer solutions are those based on citrate/HCl, borate/HCl or phosphate. The measurements were carried out from pH 4 to pH 10 in steps of one pH unit. The results of the measurement are shown in FIG. 10 and 11.

EXAMPLE 2

Production of a reference EIS structure with a phthalocyaninato-polysiloxane polymer film covered with a polyglutamate layer:

This reference electrode differs from that described in Example 1 by an additional LB film of phthalocyaninato-polysiloxane polymer. Preparation is similar to Example 1 but, before application of the polyglutamate LB film, the film balance described above is used to apply a phthalocyaninato-polysiloxane polymer film to the cleaned wafer. For this, the subphase is cooled to 6° C. and phthalocyaninato-polysiloxane polymer (degree of polymerization 100) is spread using a dilute solution (0.05%) in chloroform. After compression to 25 mN/m the film is left until it has a constant area.

The substrate is then introduced into and removed from the subphase using the film lift described above, operating at 10 mm/min. One monolayer is transferred each time thereby. After 12 monolayers had been transferred, the substrate was dried and then heated at 120° C. for 30 minutes.

30 monolayers of polyglutamate were then applied in a similar manner to Example 1. This was followed by heating, metalization, construction of the measurement cell and measurement as in Example 1. The results of measurement ar shown in FIG. 11 and 12.

We claim:

1. A reference electrode for chemical sensors based on ion-selective field-effect transistors (CHEMFETs) which contain insulator/semiconductor substrates as such or coated with thin films of phthalocyaninato-polysiloxane polymers in an electrolyte/insulator/semiconductor (EIS) system, wherein the reference electrode consists essentially of an insulator/semiconductor substrate coated with polyglutamate, or an insulator/-semiconductor substrate having thereon a phthaloxyaninato-polyisoloxane polymer film coated with polyglutamate.

2. A reference electrode as claimed in claim 1, wherein the polyglutamate has been applied by the Langmuir-Blodgett technique to the insulator/semiconductor substrate or to the phthalocyaninato-polysiloxane polymer film applied to an insulator/semiconductor substrate.

3. A reference electrode as claimed in claim 1, wherein the polyglutamate employed is a poly($\gamma$-methyl L-glutamate-co-$\gamma$-n-alkyl L-glutamate) where n-alkyl is $C_{10}H_{21}$ to $C_{25}H_{51}$ and the n-alkyl L-glutamate content is from 20 to 40%.

4. A reference electrode as claimed in claim 1, wherein the polyglutamate has been applied in a thickness of from 3.6 to 180 nm to the insulator/semiconductor substrate which is as such or has been coated with a phthalocyaninato-polysiloxane polymer film.

5. A reference electrode as claimed in claim 1, wherein an $SiO_2$/Si substrate is employed as insulator/-semiconductor substrate.

6. A reference electrode as claimed in claim 1, wherein the reference electrode is an integrated component of an $SiO_2$/Si substrate, which is as such or coated with a phthalocyaninato-polysiloxane polymer film, in an EIS system.

* * * * *